United States Patent [19]

Neustadt et al.

[11] Patent Number: 5,389,610

[45] Date of Patent: Feb. 14, 1995

[54] CARBOXYALKYLCARBONYL AMINOACID ENDOPEPTIDASE INHIBITORS

[75] Inventors: Bernard R. Neustadt, West Orange; Elizabeth M. Smith, Verona, both of N.J.; Martin F. Haslanger, Carmel, Ind.

[73] Assignee: Schering Corporation, Kenilworth, N.J.

[21] Appl. No.: 849,036

[22] PCT Filed: Nov. 20, 1990

[86] PCT No.: PCT/US90/06655

§ 371 Date: Apr. 21, 1992

§ 102(e) Date: Apr. 21, 1992

[87] PCT Pub. No.: WO91/07386

PCT Pub. Date: May 30, 1991

Related U.S. Application Data

[63] Continuation-in-part of Ser. No. 439,765, Nov. 21, 1989.

[51] Int. Cl.6 .................. C07K 5/08; A61K 39/02
[52] U.S. Cl. .................................. 514/2; 514/18; 514/19; 530/331; 530/332
[58] Field of Search ............... 514/2, 18, 19; 530/331, 530/332

[56] References Cited

U.S. PATENT DOCUMENTS

| | | | |
|---|---|---|---|
| 4,105,776 | 8/1978 | Ondetti et al. | 424/274 |
| 4,256,761 | 3/1981 | Suh et al. | 424/282 |
| 4,344,949 | 8/1982 | Hoefle et al. | 424/258 |
| 4,350,704 | 9/1982 | Hoefle et al. | 424/274 |
| 4,374,829 | 2/1983 | Harris et al. | 424/177 |
| 4,374,847 | 2/1983 | Gruenfeld | 424/274 |
| 4,410,520 | 10/1983 | Watthey | 424/244 |
| 4,462,943 | 7/1984 | Petrillo et al. | 260/112.5 |
| 4,468,519 | 8/1984 | Krapcho | 548/409 |
| 4,470,972 | 9/1984 | Gold et al. | 424/177 |
| 4,470,973 | 9/1984 | Matarajan et al. | 424/177 |
| 4,499,079 | 2/1985 | Gordon et al. | 514/2 |
| 4,508,729 | 4/1985 | Vincent et al. | 514/419 |
| 4,512,924 | 4/1985 | Attwood et al. | 260/243.3 |
| 4,513,009 | 4/1985 | Roques et al. | 514/513 |
| 4,555,506 | 11/1985 | Karanewsky et al. | 514/91 |
| 4,610,816 | 9/1986 | Berger | 549/452 |
| 4,740,499 | 4/1988 | Olins | 514/274 |

FOREIGN PATENT DOCUMENTS

| | | | |
|---|---|---|---|
| 38046 | 10/1981 | European Pat. Off. | C07C 103/52 |
| 46953 | 3/1982 | European Pat. Off. | C07D 217/26 |
| 50800 | 5/1982 | European Pat. Off. | C07C 103/52 |
| 79022 | 5/1983 | European Pat. Off. | C07D 209/52 |
| 79522 | 5/1983 | European Pat. Off. | C07C 103/52 |
| 274234 | 7/1988 | European Pat. Off. | C07C 103/737 |
| 0358398 | 8/1989 | European Pat. Off. | C07C 237/20 |
| 358398 | 3/1990 | European Pat. Off. | C07C 237/20 |
| 2095682 | 10/1982 | United Kingdom | C07C 103/52 |
| 2207351 | 2/1989 | United Kingdom | A61K 31/66 |
| 8600066 | 1/1986 | WIPO | C07C 103/52 |

OTHER PUBLICATIONS

Needleman, et al, *N. Engl. J. Med.*, 314 (1986) pp. 828–834.
Cantin, et al *Sci. Amer.*, 254 (1986) pp. 76–81.
Wyvratt, et al, *Med. Res. Rev.*, 5, 4 (1985) pp. 483–531.
Biochem. Biophys. Res. Comm., 164, (1)(1989), Academic Press, pp. 58–65.

*Primary Examiner*—Robert J. Hill, Jr.
*Assistant Examiner*—Carol Salata
*Attorney, Agent, or Firm*—Anita W. Magatti; Eric S. Dicker

[57] ABSTRACT

Carboxyalkylcarbonyl aminoacid inhibitors of endopeptidases of the formula:

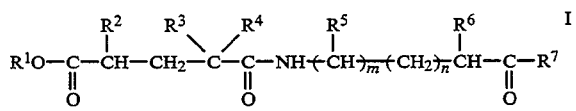

or pharmaceutically acceptable salt thereof, wherein $R^1$ is H, alkyl, arylalkyl, aryl or aryloxyalkyl; $R^2$ is alkyl, alkenyl, alkynyl, alkoxy or alkylthio, wherein the alkyl portion is substituted with 0–3 substituents independently selected from the group consisting of hydroxy, alkoxy, alkoxyalkoxy, alkylthio, aryl, alkoxyalkylthio, arylalkoxy and arylalkylthio; $R^3$ and $R^4$ are (Abstract continued on next page.)

independently alkyl or arylalkyl; or $R^3$ and $R^4$ together with the carbon to which they are attached form an optionally substituted 5-, 6- or 7-membered ring wherein said ring comprises 0 to 1 heteroatoms selected from the group consisting of sulfur and oxygen; $R^5$ is H, alkyl, alkoxyalkyl, alkylthioalkyl, aryl, arylalkyl, heteroaryl, heteroarylalkyl, arylalkoxyalkyl or arylalkylthioalkyl; $R^6$ is H, hydroxy, alkoxy, alkyl, arylalkoxy, alkoxyalkyl, alkylthioalkyl, arylalkoxyalkyl, arylalkylthioalkyl, aryl or heteroaryl; $R^7$ is hydroxy, alkoxy, aryloxy, arylalkoxy, amino, alkylamino or dialkylamino; m is 0 or 1; and n is 0, 1, 2 or 3, use of the compounds, alone or in combination with an ACE inhibitor or an ANF, in the treatment of cardiovascular disorders such as hypertension, congestive heart failure, edema and renal insufficiency, use of the compounds in the treatment of nephrotoxicity and pain conditions, and pharmaceutical compositions containing said compounds are disclosed.

8 Claims, No Drawings

CARBOXYALKYLCARBONYL AMINOACID ENDOPEPTIDASE INHIBITORS

The present application is the U.S. national application corresponding to International Application No. PCT/US 90/06,655, filed Nov. 20, 1990, and designating the United States, which PCT application is in turn a continuation-in-part of U.S. application Ser. No. 439,765, filed Nov. 21, 1989, the benefit of which applications is claimed pursuant to the provisions of 35 U.S.C. §§120,363 and 365(C).

BACKGROUND OF THE INVENTION

The present invention relates to carboxyalkylcarbonyl aminoacid inhibitors of endopeptidases useful in the treatment of cardiovascular disorders, nephrotoxicity and pain conditions.

Cardiovascular conditions which may be treated with compounds of the present invention include hypertension, congestive heart failure, edema and renal insufficiency. Nephrotoxicity resulting from immunosuppression therapy may also be treated with compounds of this invention.

Human hypertension is a disease of multiple etiologies. Included among these is a sodium and volume dependent low renin form of hypertension. Drugs that act to control one aspect of hypertension will not necessarily be effective in controlling another.

Enkephalin is a natural opiate receptor agonist which is known to produce a profound analgesia when injected into the brain ventricle of rats. Enkephalin is known to be inactivated by a group of naturally occurring enzymes known as enkephalinases or endopeptidases.

A variety of compounds known as endopeptidase inhibitors are useful as analgesics and/or in the treatment of hypertension. For example, European Patent Application 274,234 discloses, inter alia, spiro-substituted glutaramide diuretic compounds of the formula

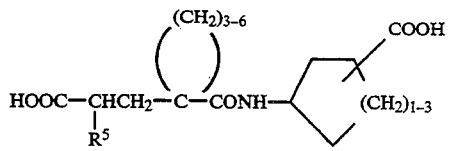

wherein $R^5$ may be a variety of alkyl or amino derivatives or a heterocycle. European Patent Application 358,398 discloses similar compounds wherein the carboxy-substituted cycloalkylamino group is replaced by a substituted alanyl group, e.g. phenylalanyl.

European Patent Application 38,046 discloses, inter alia, enkephalinase inhibitors of the formula

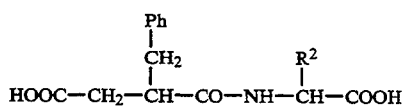

wherein $R^2$ is lower alkyl or methylthiomethyl and Ph is optionally substituted phenyl.

U.S. Pat. No. 4,513,009 discloses, inter alia, alpha amino acid derivatives of the formula

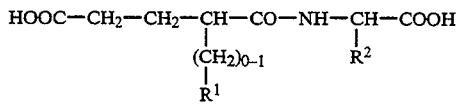

wherein $R^1$ is preferably hydrogen or phenyl and $R^2$ is preferably hydrogen, alkyl, benzyl or benzyloxyalkyl. The compounds are said to have enkephalinase inhibiting and hypotensive activity.

U.S. Pat. No. 4,939,261 discloses enkephalinase inhibitory N-substituted butyramide derivatives of the formula

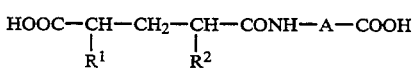

wherein $R^1$ and $R^2$ are alkyl or arylalkyl and A is alkylene, substituted alkylene, phenylene or cyclohexylene.

U.S. Pat. No. 4,610,816 discloses, inter alia, substituted dipeptide enkephalinase inhibitors of the formula

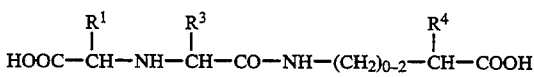

wherein $R^1$ and $R^3$ are preferably phenylethyl and $R^4$ is preferably hydrogen, methyl or benzyl.

Similarly, German Patent Application 3,819,539 discloses, inter alia, carboxyalkyl compounds of the formula

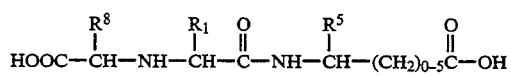

wherein $R_1$ and $R_8$ are preferably benzyl and $R_5$ is preferably hydrogen or lower alkyl.

It has recently been discovered that the heart secretes a series of peptide hormones called atrial natriuretic factors (ANF) which help to regulate blood pressure, blood volume and the excretion of water, sodium and potassium. ANF were found to produce a short-term reduction in blood pressure and to be useful in the treatment of congestive heart failure. See P. Needleman et al, "Atriopeptin: A Cardiac Hormone Intimately Involved in Fluid, Electrolyte and Blood-Pressure Homostasis", *N. Engl. J. Med.*, 314, 13 (1986) pp. 828–834, and M. Cantin et al in "The Heart as an Endocrine Gland", *Scientific American*, 254 (1986) pg. 76–81.

Angiotensin converting enzyme (ACE) inhibitors are another class of drugs known to be effective in treating some types of hypertension. ACE inhibitors are useful in blocking the rise in blood pressure caused by increases in vascular resistance and fluid volume due to the formation of angiotensin II from angiotensin I. For a review of ACE inhibitors, see M. Wyvratt et al., "Recent Developments in the Design of Angiotensin Converting Enzyme Inhibitors" in *Med. Res. Rev.*, 5, No. 4 (1985) pp. 483–531.

SUMMARY OF THE INVENTION

Novel compounds of the present invention are represented by the formula

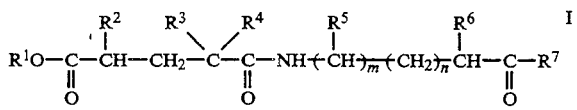

wherein
- R[1] is H, alkyl, arylalkyl, aryl or aryloxyalkyl;
- R[2] is alkyl, alkenyl, alkynyl, alkoxy or alkylthio, wherein the alkyl portion is substituted with 0-3 substituents independently selected from the group consisting of hydroxy, alkoxy, alkoxyalkoxy, alkylthio, aryl, alkoxyalkylthio, arylalkoxy and arylalkylthio;
- R[3] and R[4] are independently alkyl or arylalkyl; or R[3] and R[4] together with the carbon to which they are attached form a 5-, 6- or 7-membered ring wherein said ring comprises 0 to 1 heteroatoms selected from the group consisting of sulfur and oxygen, wherein said ring is unsubstituted or is substituted on a carbon atom ring member by an alkyl or aryl group, or wherein said ring is substituted by a fused benzene ring;
- R[5] is H, alkyl, alkoxyalkyl, alkylthioalkyl, aryl, arylalkyl, heteroaryl, heteroarylalkyl, arylalkoxyalkyl or arylalkylthioalkyl;
- R[6] is H, hydroxy, alkoxy, alkyl, arylalkoxy, alkoxyalkyl, alkylthioalkyl, arylalkoxyalkyl, arylalkylthioalkyl, aryl or heteroaryl;
- R[7] is hydroxy, alkoxy, aryloxy, arylalkoxy, amino, alkylamino or dialkylamino;
- m is 0 or 1;
- n is 0, 1, 2 or 3;

or a pharmaceutically acceptable salt thereof.

A preferred group of compounds of the present invention is that wherein R[2] is arylalkyl, especially phenylethyl, or alkoxyalkoxyalkyl, especially methoxyethoxymethyl. Another preferred group is that wherein R[3] and R[4] together with the carbon to which they are attached form a 5-, 6- or 7-membered ring, especially a carbocyclic ring; especially preferred is a 5-membered ring. Still another preferred group in that wherein R[5] is hydrogen, R[6] is hydroxy or hydrogen, m is 1 and n is zero. Also preferred are compounds wherein R[6] is alkylthioalkyl and m and n are each zero; an especially preferred alkylthioalkyl group is methylthioethyl.

Other preferred compounds of formula I are those wherein R[1] is hydrogen. R[7] is preferably hydroxy, ethoxy or benzyloxy.

The invention also relates to the treatment of cardiovascular diseases or nephrotoxicity with a combination of a carboxyalkylcarbonyl aminoacid of the present invention and an atrial natriuretic factor (ANF) or with a combination of a carboxyalkylcarbonyl aminoacid of the present invention and an angiotensin converting enzyme (ACE) inhibitor.

Other aspects of the invention relate to pharmaceutical compositions comprising a carboxyalkylcarbonyl aminoacid of this invention, alone or in combination with an ANF or an ACE inhibitor, and to methods of treatment of cardiovascular diseases comprising administering a carboxyalkylcarbonyl aminoacid of this invention, alone or in combination with an ANF or an ACE inhibitor, to a mammal in need of such treatment.

Still another aspect of this invention relates to a method of treating pain conditions by administering a carboxyalkylcarbonyl aminoacid of this invention, thereby inhibiting the action of endopeptidases in a mammal and eliciting an analgesic effect. Analgesic pharmaceutical compositions comprising said carboxyalkylcarbonyl aminoacid compounds are also contemplated.

DETAILED DESCRIPTION

As used herein, the term "alkyl" means straight or branched lower alkyl chains of 1 to 6 carbon atoms; "alkenyl" similarly means lower alkenyl chains of 2 to 6 carbon atoms; "alkynyl" means lower alkynyl chains of 2 to 6 carbon atoms; and "alkoxy" similarly means lower alkoxy chains of 1 to 6 carbon atoms.

"Aryl" means a phenyl or naphthyl ring; a phenyl or naphthyl ring substituted with 1-3 substituents selected from the group consisting of alkyl, hydroxy, alkoxy, halo, trifluoromethyl, phenyl, phenoxy and phenylthio; or a phenyl ring wherein adjacent alkyl or alkyl and alkoxy substituents form a 5- or 6-membered ring (for example indanyl, dihydrobenzofuranyl, 1,2,3,4-tetrahydronaphthyl and isochromanyl).

"Heteroaryl" means mono-cyclic or fused ring bicyclic aromatic groups having 5 to 10 ring members wherein 1-2 ring members are independently selected from the group consisting of oxygen, nitrogen and sulfur and wherein 1-3 carbon ring members may be substituted with substituents as defined above for aryl. Examples of heteroaryl groups are furanyl, thienyl, pyrrolyl, benzofuranyl, thianaphthenyl, indolyl and pyridyl.

All positional isomers of the aryl and heteroayl groups are contemplated, e.g. 2-pyridyl and 3-pyridyl, α-naphthyl and β-naphthyl.

Halo means fluoro, chloro, bromo or iodo radicals.

Certain compounds of the invention are acidic e.g., those compounds which possess a carboxyl group. These compounds form pharmaceutically acceptable salts with inorganic and organic bases. Examples of such salts are the sodium, potassium, calcium and aluminum salts. Also included are salts formed with pharmaceutically acceptable amines such as ammonia, alkyl amines, hydroxy alkyl amines, N-methylglucamine and the like.

The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Compounds of formula I have at least one asymmetrical carbon atom and therefore include various stereoisomers. The invention includes all such isomers both in pure form and in admixture, including racemic mixtures.

An aspect of the present invention described above relates to the combination of a compound of formula I with an ANF. As indicated by Needleman et al., a number of ANF have been isolated so far, all having the same core sequence of 17 amino acids within a cystsine disulfide bridge, but having different N-termini lengths. These peptides represent N-terminal truncated fragments (21–48 amino acids) of a common preprohormone (151 and 152 amino acids for man and rats, respectively). Human, porcine and bovine carboxy-terminal 28-amino acid peptides are identical and differ from similar peptides in rats and mice in that the former contain a methionine group at position 12 while the latter contain isoleucine. Various synthetic analogs of naturally occurring ANF's also have been found to have comparable biological activity. Examples of ANF's contemplated for use in this invention are α human AP 21 (atriopeptin I), α human AP 28, α human AP 23 (atriopeptin II or APII), α human AP 24, α human AP 25, α human AP 26, α human AP 33, and the corresponding rat sequence of each of the above wherein Met 12 is Ile.

Another aspect of the invention is the administration of a combination of an ACE inhibitor and a compound of formula I.

Examples of ACE inhibitors are those disclosed in the article by Wyvratt et al., cited above, and in the following U.S. patents: U.S. Pat. Nos. 4,105,776, 4,468,519, 4,555,506, 4,374,829, 4,462,943, 4,470,973, 4,470,972, 4,350,704, 4,256,761, 4,344,949, 4,508,729, 4,512,924, 4,410,520 and 4,374,847, all incorporated herein by reference; and the following foreign patents or published patent applications:

British Specification No. 2095682 published Oct. 6, 1982 discloses N-substituted-N-carboxyalkylcarbonyl amino carboxyl alkyl glycine derivatives which are said to be angiotensin converting enzyme inhibitors and have the formula

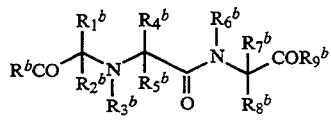

either (A)

$R^b$ and $R_9^b$ are OH, 1–6C alkoxy, 2–6C alkonyloxy, di- (1–6C alkyl) amino-(1–6C) alkoxy, 1–6C hydroxy alkoxy, acylamino- (1–6C) alkoxy, acyloxy-(1–6C) alkoxy, aryloxy, aryloxy-(1–6C)alkoxy, $NH_2$, mono- or di-(1–6C alkyl)amino, hydroxy amino or aryl-(1–6C)alkylamino; $R_1^b$–$R_5^b$, $R_7^b$ and $R_8^b$ are 1–20C alkyl, 2–20C alkonyl, 2–20C alkynyl, aryl, aryl-(1–6C) alkyl having 7–12C or heterocyclyl-(1–6C)alkyl having 7–12C;

$R_6^b$ is cycloalkyl polycycloalkyl partly saturated cycloalkyl or polycycloalkyl, cycloalkyl-(1–6C) alkyl having 3–20C, 6–10C aryl, aryl-(1–6C)alkyl, aryl-(2–6C)alkenyl or aryl-(2–6C) alkynyl; or $R_2^b$ and $R_3^b$ together with the C and N atoms to which they are attached or $R_3^b$ and $R_5^b$ together with the N and C atoms to which they are attached form an N-heterocycle containing 3–5C or 2–4C and a S atom;

all alkyl, alkonyl and alkynyl are optionally substituted by OH, 1–6C alkoxy, thio(sic), 1–6C alkylthio, $NH_2$, mono- or di (1–6C alkyl) amino, halogen or $NO_2$;

all 'cycloalkyl' groups (including poly and partially unsaturated) are optionally substituted by halogen, 1–6C hydroxy alkyl, 1–6C alkoxy, amino-(1–6C alkyl)amino, di-(1–6C alkyl) amino, SH, 1–6C alkylthio, $NO_2$ or $CF_3$; and aryl groups are optionally substituted by OH, 1–6C alkoxy, $NH_2$, mono- or di-(1–6C alkyl) amino, SH, 1–6C alkylthio, 1–6C hydroxy alkyl, 1–6C aminoalkyl, 1–6C thioalkyl, $NO_2$, halogen, $CF_3$, $OCH_2O$, ureido or guanidino; or (B)

$R^b$ and $R_9^b$ are H or 1–6C alkoxy;

$R_1^b$ and $R_2^b$ are H, 1–6C alkyl, aryl-(1–6C) alkyl having 7–12C or heterocyclyl-(1–6C) alkyl having 6–12C;

$R_3^b$–$R_5^b$, $R_7^b$ and $R_8^b$ are H or 1–6C alkyl;

$R_6^b$ is cycloalkyl, polycycloalkyl, partly saturated cycloalkyl or polycycloalkyl, cycloalkyl-(1–6C) alkyl having 3–20C, aryl or aryl-(1–6C) alkyl; and aryl has 6–10C and is optionally substituted by 1–6C alkyl, 2–6C alkonyl, 2–6C alkynyl, OH, 1–6C alkoxy, $NH_2$, mono- or di-(1–6C alkyl) amino, SH, 1–6C alkylthio, 1–6C hydroxy alkyl, 1–6C aminoalkyl, 1–6C thioalkyl, $NO_2$, halogen, $CF_3$, $OCH_2O$, ureido or guanidino;

European Patent Application 0 050 800 published May 5, 1982 discloses carboxy alkyl dipeptides derivatives which are said to be angiotensin converting enzyme inhibitors and have the formula

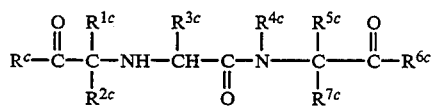

or a pharmaceutically acceptable salt thereof, wherein $R^c$ and $R^{6c}$ are the same or different and are hydroxy, lower alkoxy, lower alkonyloxy, dilower alkylamino lower alkoxy, acylamino lower alkoxy, acyloxy lower alkoxy, aryloxy, aryllower alkoxy, amino, lower alkylamino, dilower alkylamino, hydroxy amino, aryllower alkylamino, or substituted aryloxy or substituted aryllower alkoxy wherein the substituent is methyl, halo or methoxy; $R^{1c}$ is hydrogen, alkyl of from 1 to 10 carbon atoms, substituted lower alkyl wherein the substituent is hydroxy, lower alkoxy, aryloxy, substituted aryloxy, heteroaryloxy, substituted heteroaryloxy, amino, lower alkylamino, diloweralkylamino, acylamino, arylamino, substituted arylamino,,guanidino, imidazolyl, indolyl, lower alkylthio, arylthio, substituted arylthio, carboxy, carbamoyl, lower alkoxy carboxyl, aryl, substituted aryl, aralkyloxy, substituted aralkyloxy, aralkylthio or substituted aralkylthio, wherein the aryl or heteroaryl portion of said substituted aryloxy, heteroaryloxy, arylamino, arylthio, aryl, aralkyloxy, aralkylthio group is substituted with a group selected from halo, lower alkyl, hydroxy, lower alkoxy, amino, aminomethyl, carboxyl, cyano, or sulfamoyl; $R^{2c}$ and $R^{7c}$ are the same or different and are hydrogen or lower alkyl; $R^{3c}$ is hydrogen, lower alkyl, phenyl lower alkyl, aminoethylphenyl lower alkyl, hydroxyphenyl lower alkyl, hydroxy lower alkyl, acylamino lower alkyl, amino lower alkyl, dimethylamino lower alkyl, guanidino lower alkyl, imidazolyl lower alkyl, indolyl lower alkyl, or lower alkyl thio lower alkyl; $R^{4c}$ and $R^{5c}$ are the same or different and are hydrogen, lower alkyl or $Z^c$, or $R^{4c}$ and $R^{5c}$ taken together form a group represented by $Q^c$, $U^c$, $v^c$, $Y^c$, $D^c$ $E^c$, wherein; or $Z^c$ is

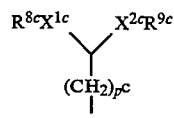

wherein $X^{1c}$ and $X^{2c}$ independent of each other are O, S or $CH_2$, $R^{8c}$ and $R^{9c}$ independent of each other are lower alkyl, lower alkonyl, lower alkynyl, cycloalkyl having 3 to 8 carbon atoms, hydroxy lower alkyl, or —$(CH_2)_{n^c}Ar^c$, wherein $n^c$ is 0, 1, 2 or 3 and $Ar^c$ is unsubstituted or substituted phenyl, furyl, thienyl or pyridyl, wherein said substituted phenyl, furyl, thienyl or pyridyl groups are substituted with at least one group that is independently selected from $C_1$ to $C_4$ alkyl, lower alkoxy, lower alkylthio, halo, $CF_3$ and hydroxy, or $R^{8c}$ and $R^{9c}$ taken together form a bridge $W^c$, wherein $W^c$ is a single bond or a methylene bridge or a substituted methylene bridge when at least one of $X^{1c}$ and $X^{2c}$ is methylene, or $W^c$ is an alkylene or substituted alkylene bridge having 2 or 3 carbon atoms, said substituted methylene bridge or said substituted alkylene bridge having one or two substituents selected from lower alkyl, aryl and aryl lower alkyl groups, and $p^c$ is 0, 1 or 2; with the proviso that at least one of $R^{4c}$ and $R^{5c}$ is $Z^c$, with the proviso that if $R^{4c}$ is $Z^c$ and $p^c$ is 0 then $X^{1c}$ and $X^{2c}$ must both be methylene, and with the proviso that if $X^{1c}$ and $X^{2c}$ are both methylene then $R^{8c}$ and $R^{9c}$ must form an alkylene bridge $W^c$;

$Q^c$ is

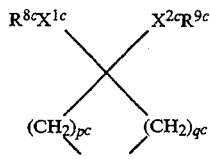

wherein $R^{8c}$, $R^{9c}$, $X^{1c}$ and $X^{2c}$ are as defined above, $p^c$ is 0, 1 or 2,, $q^c$ is 0, 1 or 2, with the proviso that the sum of $p^c$ and $q^c$ must be 1, 2 or 3, with the proviso that if $p^c$ is 0 then $X^{1c}$ and $X^{2c}$ must be methylene, and with the proviso that if $X^{1c}$ and $X^{2c}$ are methylene then $R^{8c}$ and $R^{9c}$ taken together form a bridge $W^c$, wherein $W^c$ is as defined above;

$V^c$ is

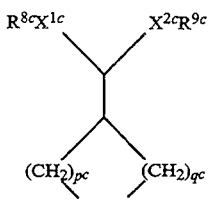

wherein $R^{8c}$, $R^{9c}$, $X^{1c}$ and $X^{2c}$ are as defined above, $p^c$ is 0, 1 or 2 and $q^c$ is 0, 1 or 2, with the proviso that the sum of $p^c$ and $q^c$ is 1, 2 or 3, with the proviso that if $X^{1c}$ and $X^{2c}$ are $CH_2$ then $R^{8c}$ and $R^{9c}$ taken together form a bridge $W^c$, wherein $W^c$ is as defined above;

$U^c$ is

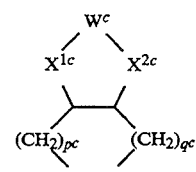

wherein $W^c$ is as defined above (except that $W^c$ may also be a methylene bridge when $X^{1c}$ and $X^{2c}$ are oxygen or sulfur), $X^{1c}$ and $X^{2c}$ are as defined above, $p^c$ is 0, 1 or 2, $q^c$ is 0, 1 or 2, with the proviso that the sum of $p^c$ and $q^c$ is 1 or 2, and with the proviso that if $p^c$ is 0, $X^{1c}$ must be $CH_2$;

$y^c$ is

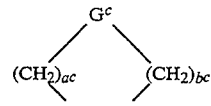

wherein $G^c$ is oxygen, sulfur or $CH_2$, $a^c$ is 2 3 or 4 and $b^c$ is 1, 2, 3, 4 or 5, with the proviso that the sum of $a^c$ and $b^c$ is 5, 6 or 7 or $G^c$ is $CH_2$, $a^c$ is 0, 1, 2 or 3 $b^c$ is 0 1 2 or 3 with the proviso that the sum of $a^c$ and $b^c$ is 1, 2 or 3, with the proviso that the sum of $a^c$ and $b^c$ may be 1, 2 or 3 only if $R^{1c}$ is lower alkyl substituted with aralkylthio or aralkyloxy;

$D^c$ is

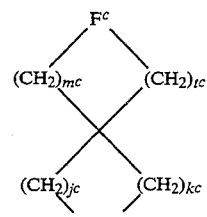

wherein $F^c$ is O or S, $j^c$ is 0, 1 or 2 and $k^c$ is 0, 1 or 2, with the proviso that the sum of $j^c$ and $k^c$ must be 1, 2 or 3, and $m^c$ is 1, 2 or 3 and $t^c$ is 1,-2 or 3, with the proviso that the sum of $m^c$ and $t^c$ must be 2, 3 or 4;

$E^c$ is

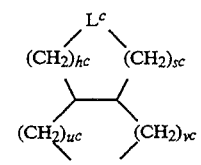

wherein $L^c$ is O or S, $u^c$ is 0 1 or 2 and $v^c$ is 0, 1 or 2, with the proviso that the sum of $u^c$ and $v^c$ must be 1 or 2, and $h^c$ is 1 or 2 and $s^c$ is 1 or 2, with the proviso that the sum of $h^c$ and $s^c$ must be 2 or 3;

European Patent Application 0 079 522 published May 25, 1983 discloses N-carboxymethyl(amidino)-lysylproline compounds which are said to be angiotensin converting enzyme inhibitors and have the formula where

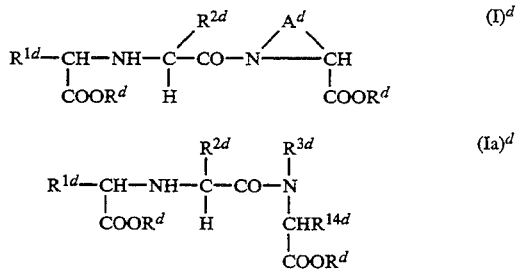

wherein:

$R^d$ and $R^{2d}$ are independently hydrogen; loweralkyl; aralkyl; or aryl;

$R^{1d}$ is hydrogen; branched or straight chain $C_{1-12}$ alkyl and alkonyl; $C_3-C_9$ cycloalkyl and benzofused alkyl; substituted loweralkyl where the substituents are halo, hydroxy loweralkoxy, aryloxy, amino, mono- or diloweralkylamino, acylamino, arylamino, guanidino, mercapto, loweralkylthio, arylthio, carboxy, carboxamido, or loweralkoxycarbonyl; aryl; substituted aryl where the substituents are loweralkyl, loweralkoxy, or halo; arloweralkyl; arloweralkenyl; heteroarloweralkyl; heteroarloweralkenyl; substituted arloweralkyl, substituted arloweralkenyl, substituted heteroarloweralkyl, or substituted heteroarloweralkenyl where the aryl and heteroaryl substituents are halo, dihalo, loweralkyl, hydroxy, loweralkoxy, amino, aminoloweralkyl, acylamino, mono- or diloweralkylamino, carboxyl, haloloweralkyl, nitro, cyano, or sulfonamido, and where the loweralkyl portion of arloweralkyl may be substituted by amino, acylamino, or hydroxyl;

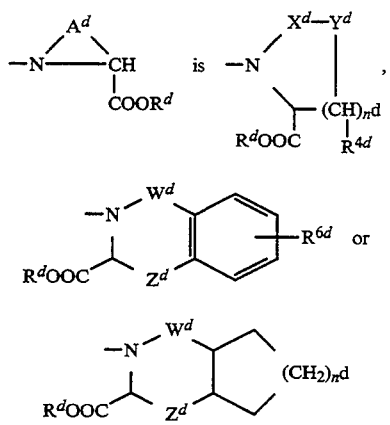

where:
$X^d$ and $Y^d$ taken together are —CH$_2$—CH$_2$—;

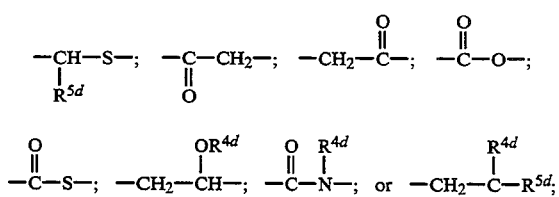

$R^{4d}$ is hydrogen; loweralkyl; aryl; substituted aryl;
$R^{5d}$ is hydrogen; loweralkyl; aryl or substituted aryl;
$n^d$ is 1 to 3;
$W^d$ is absent; —CH$_2$—; or

$Z^d$ is —(CH$_2$)$_{m^d}$, where $m^d$ is 0 to 2, provided that $m^d$ may not be 0 and $W^d$ may not be absent at the same time; and $R^{6d}$ is hydrogen; loweralkyl; halo; or $OR_{4d}$;
$R^{2d}$ is —(CH$_2$)$_{r^d}$1'B$^d$—(CH$_2$)$_{s^d}$—NR$^{7d}$R$^{15d}$
where
$r^d$ and $s^d$ are independently 0 to 3;

$B^d$ is absent; —O—; —S—; or —NR$^{8d}$; where R$^{8d}$ is hydrogen; loweralkyl; alkanoyl; or aroyl; and

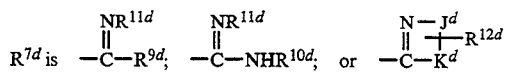

where
$R^{9d}$ is loweralkyl; aralkyl; aryl; heteroaryl; or heteroarloweralkyl and these groups substituted by hydroxy, lower alkoxy or halo; carboxyl; carboxamido; nitromethenyl.
$R^{10d}$ is hydrogen; loweralkyl; aryl; or amidino;
$R^{11d}$ hydrogen; loweralkyl; cyano; amidino; aryl; aroyl; loweralkanoyl;

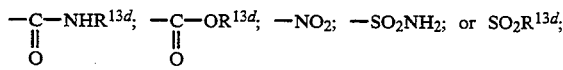

$R^{12d}$ is hydrogen; loweralkyl; halo; aralkyl; amino; cyano; mono- or diloweralkylamino; or $OR^{4d}$;
$R^{13d}$ hydrogen; loweralkyl; or aryl;
$R^{15d}$ hydrogen; lower alkyl; aralkyl; or aryl;

constitute a basic heterocycle of 5 or 6 atoms or benzofused analogs thereof and optionally containing 1-3 N atoms, an oxygen, a sulfur, an S=O, or an SO$_2$ group optionally substituted by amino, lower alkyl amino, diloweralkyl amino, lower alkoxy, or aralkyl groups;

$R^{3d}$ is $C_{3-8}$ cycloalkyl and benzofused $C_{3-8}$ cycloalkyl; perhydrobenzofused $C_{3-8}$ cycloalkyl; aryl; substituted aryl; heteraryl; substituted heteroaryl;
$R^{14d}$ is hydrogen or loweralkyl; and, a pharmaceutically acceptable salt thereof;

European Patent 79022 published May 18, 1983 discloses N-amino acyl-azabicyclooctane-carboxylic acid derivatives which have the formula

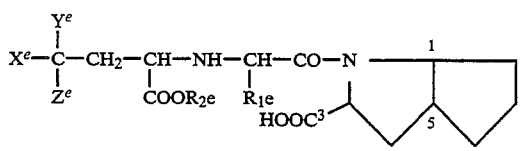

hydrogen atoms at ring positions 1 and 5 are cis to each other and the 3-carboxy group has the endo orientation;

$R_1^e$ is H, allyl, vinyl or the side chain of an optionally protected naturally occurring α-amino acid;
$R_2^e$ is H, 1–6C alkyl, 2–6C alkonyl or aryl(1–4C alkyl);
$Y^e$ is H or OH and $Z^e$ is H, or ye and $Z^e$ together oxygen;
$X^e$ is 1–6C alkyl, 2–6C alkonyl, 5–9C cycloalkyl, 6–12C aryl (optionally substituted by one to three 1–4C alkyl or alkoxy, OH, halo, nitro, amino (optionally substituted by one or two 1–4C alkyl), or methylenedioxy) or indol-3-yl);

European Patent 46953 published March 10, 1982 discloses N-amino acyl-indoline and tetrahydro isoquinoline carboxylic acids which are angiotensin coverting enzyme inhibitors and have the formula

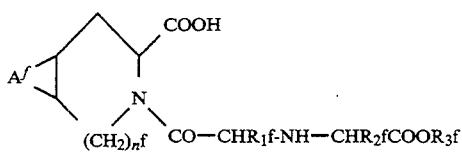

$n^f$ is 0 or 1;

is a benzene or cyclohexane ring:

$R_1^f$ and $R_2^f$ are each 1-6C alkyl, 2-6C alkonyl, 5-7C cycloalkyl, 5-7C cycloalkenyl, 7-12C cycloalkylalkyl, optionally partially hydrogenated 6-10C aryl, 7-14C aralkyl or 5-7 membered monocyclic or 8-10 membered bicyclic heterocyclyl containing 1 or 2 S or O and/or 1-4N atoms; all $R_1^f$ add $R_2^f$ groups are optionally substituted, $R_3^f$ is H 1-6C alkyl, 2-6C alkonyl or 7-14C aralkyl.

The following Table II lists ACE inhibitors preferred for use in the combination of this invention.

TABLE II
PREFERRED ACE INHIBITORS $$\begin{array}{c} COOR^1 \quad R^2 \quad O \\ | \quad\quad\quad | \quad\quad || \\ R-CH-NH-CH-C-R^3 \end{array}$$

| | R | $R_1$ | $R_2$ | $R_3$ |
|---|---|---|---|---|
| spirapril | $C_6H_5CH_2CH_2-$ | Et | $CH_3$ | (S,S-containing N-C-COOH ring) |
| enalapril | $C_6H_5CH_2CH_2-$ | Et | $CH_3$ | prolyl |
| ramipril | $C_6H_5CH_2CH_2-$ | Et | $CH_3$ | (bicyclic N-C-COOH) |
| perindopril | $CH_3CH_2CH_2$ | Et | $CH_3$ | (cyclohexane-fused N-C-COOH) |
| indolapril | $C_6H_5CH_2CH_2-$ | Et | $CH_3$ | (cyclohexane-fused N-C-COOH) |
| lysinopril | $C_6H_5CH_2CH_2-$ | H | $NH_2(CH_2)_4-$ | prolyl |
| quinapril | $C_6H_5CH_2CH_2-$ | Et | $CH_3$ | (benzo-fused N-C-COOH) |
| pentopril (NH = $CH_2$) | $CH_3$ | Et | $CH_3$ | (benzo-fused N-C-COOH) |

TABLE II-continued

PREFERRED ACE INHIBITORS

| | | | |
|---|---|---|---|
| cilazapril | $C_6H_5CH_2CH_2-$ | H | $\begin{array}{cc} R_2 & O \\ | & \| \\ CH-C-R_3 \end{array}$ |

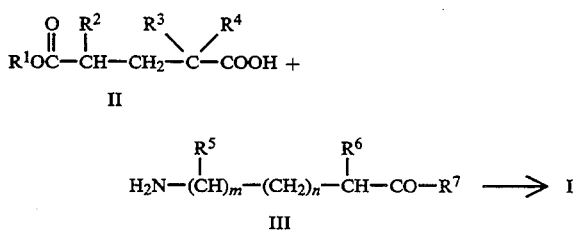

$$RS-CH_2-\underset{\underset{CH_3}{|}}{CH}-\overset{\overset{O}{\|}}{C}-R^2$$

| | R | | $R_2$ |
|---|---|---|---|
| captopril | H | | prolyl |
| zofenopril | $C_6H_5CO-$ | | $-N\!\!-\!\!\!-\!\!\!-\!\!\!\overset{SC_6H_5}{\underset{}{C}}-COOH$ |
| pivalopril | $(CH_3)_3C-\overset{\overset{O}{\|}}{C}-$ | | $-N-CH_2-COOH$ (cyclopentyl) |

$$R-\overset{\overset{O}{\|}}{\underset{\underset{OR^1}{|}}{P}}-CH_2-\overset{\overset{O}{\|}}{C}-N\!\!-\!\!\!-\!\!\!-\!\!\!\overset{R^2}{\underset{}{C}}-COOH$$

| | R | $R^1$ | $R^2$ |
|---|---|---|---|
| fosinopril | $C_6H_5-(CH_2)_4-$ | $\begin{array}{c}(CH_3)_2\\|\\CH\\|\\-CH-O-\underset{\underset{O}{\|}}{C}-CH_2CH_3\end{array}$ | $C_6H_5-$ |

The compounds of the present invention can be produced by methods known to those skilled in the art, for example by one or more of the methods described below. Reactive groups not involved in the condensations described below, e.g., carboxy, etc., may be protected by methods standard in peptide chemistry prior to the coupling reactions and subsequently deprotected to obtain the desired products. In the formulae in the following description of the processes, $R^1$, $R^2$, $R^3$, $R^4$, $R^5$, $R^6$ and $R^7$ are as defined above for Formula I, including suitable protection where appropriate.

An acid of formula II can be condensed with an amine of formula III:

$$R^1O\overset{\overset{O}{\|}}{C}-\underset{\underset{}{|}}{\overset{\overset{R^2}{|}}{CH}}-CH_2-\underset{}{\overset{R^3 \; R^4}{\overset{\diagdown\diagup}{C}}}-COOH \;+$$

II $$H_2N-(CH)_m-(CH_2)_n-\underset{\underset{}{|}}{\overset{\overset{R^5}{|}}{\phantom{C}}}\,\,\,\underset{}{\overset{\overset{R^6}{|}}{CH}}-CO-R^7 \longrightarrow I$$

III wherein $R^1$ to $R^7$, m and n are as defined for formula I. This reaction is well known from peptide chemistry. The reaction can be carried out in the presence of a condensing agent such as 1-(3-dimethylaminopropyl)-3-ethyl-carbodiimide hydrochloride (DEC), dicyclohexylcarbodiimide (DCC), diphenylphosphoryl azide (DPPA) or N,N-disuccinimidyl carbonate in an inert solvent such as dimethylformamide. While, as mentioned above, reactive groups are protected before the coupling reaction is carried out, the carboxy group of compound II can be activated via the intermediacy of active esters such as that derived from 1-hydroxybenzotriazole, its mixed anhydride (derived from a chlorocarbonic acid ester) or its azide.

It is evident that a compound of formula I obtained by the above process can be transferred into another compound of formula I by methods known in the art.

The starting compounds in this reaction are known compounds and/or can be prepared according to known methods. The compound of formula II can, for example, be prepared by alkylation of a dianion of formula IV with an electrophilic agent, e.g., a compound of formula V or VI:

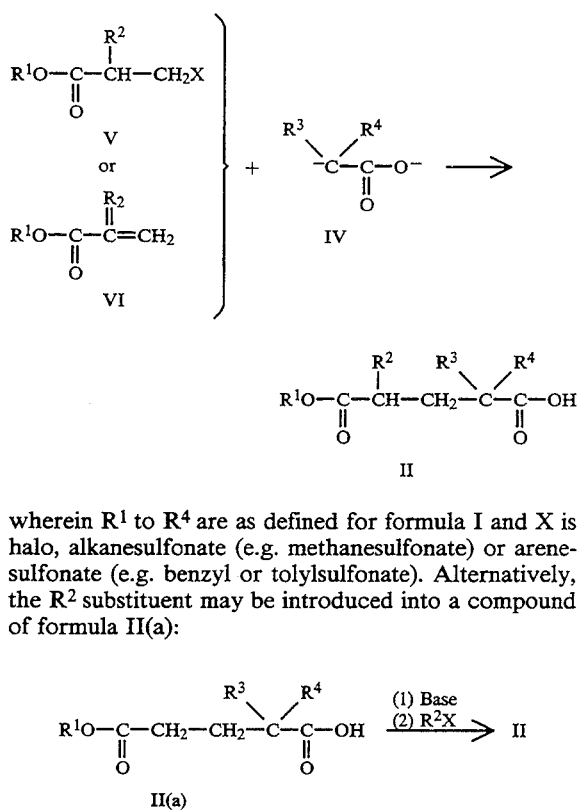

wherein $R^1$ to $R^4$ are as defined for formula I and X is halo, alkanesulfonate (e.g. methanesulfonate) or arenesulfonate (e.g. benzyl or tolylsulfonate). Alternatively, the $R^2$ substituent may be introduced into a compound of formula II(a):

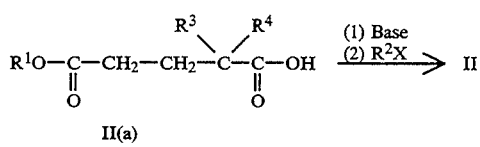

In the above scheme, $R^1$ to $R^4$ are as defined for formula I, X is as defined above and suitable bases are strong bases such as lithium diisopropylamide (LDA), sodium hexamethyl disilazide and lithium tetramethyl piperidine. These processes can be carried out in an inert solvent such as THF at temperatures from $-78°$ C. to room temperature.

The above processes can be followed by removing protecting groups by known methods. Protected carboxy groups, e.g. when $—OR^1$ and $R^7$ are alkoxy (e.g., methoxy, ethoxy, or tert. butyloxy), nitrobenzyloxy or benzyloxy, are deprotected by hydrolysis or hydrogenation. Hydrolysis can be carried out under acidic conditions (using e.g. a halogen hydracid or trifluoroacetic acid) or under basic conditions. For example, hydrolysis of a benzyl ester of formula I wherein $R^7$ is benzyloxy and $R^1$ is alkyl will yield compounds of formula I wherein $R^1$ is alkyl and $R^7$ is hydroxy; compounds wherein $R^7$ is alkoxy and $R^1$ is alkyl will yield compounds of formula I wherein $R^1$ is hydrogen and $R^7$ is alkoxy upon acid hydrolysis, and subsequent basic hydrolysis will yield compounds wherein $R^7$ is hydroxy.

We have found that the novel compounds of the present invention are effective in treating cardiovascular disorders such as congestive heart failure, edema, renal insufficiency and various types of hypertension, particularly volume expanded hypertension. These novel compounds enhance both the magnitude and duration of the antihypertensive and natriuretic effects of endogenous ANF. Administration of a combination of a carboxyalkylcarbonyl aminoacid and an ACE inhibitor provides an antihypertensive effect greater than either the carboxyalkylcarbonyl aminoacid or ACE inhibitor alone. Administration of a combination of a carboxyalkylcarbonyl aminoacid of formula I and an exogenous ANF or ACE inhibitor is therefore particularly useful in treating hypertension or congestive heart failure.

In addition to the compound aspect, the present invention therefore also relates to treating cardiovascular disorders with a carboxyalkylcarbonyl aminoacid of formula I or with a carboxyalkylcarbonyl aminoacid of formula I in combination with an ANF or an ACE inhibitor, which methods comprise administering to a mammal in need of such treatment an amount of the carboxyalkylcarbonyl aminoacid or an amount of a combination of a carboxyalkylcarbonyl aminoacid and ANF or ACE inhibitor effective to treat hypertension, congestive heart failure, edema or renal insufficiency. The drug or combination of drugs is preferably administered in a pharmaceutically acceptable carrier, e.g. for oral or parenteral administration. The combinations of drugs may be co-administered in a single composition, or components of the combination therapy may be administered separately. Where the components are administered separately, any convenient combination of dosage forms may be used, e.g. oral carboxyalkylcarbonyl aminoacid/oral ANF, oral carboxyalkylcarbonyl aminoacid/ parenteral ACE inhibitor, parenteral carboxyalkylcarbonyl aminoacid/oral ANF, parenteral carboxyalkylcarbonyl aminoacid/parenteral ACE inhibitor.

When the components of a combination of a carboxyalkylcarbonyl aminoacid and an ANF are administered separately, it is preferred that the carboxyalkylcarbonyl aminoacid be administered first.

The present invention also relates to a pharmaceutical composition comprising a carboxyalkylcarbonyl aminoacid for use in treating hypertension, congestive heart failure,edema or renal insufficiency, to a pharmaceutical composition comprising both a carboxyalkylcarbonyl aminoacid and an ANF and to a pharmaceutical composition comprising both a carboxyalkylcarbonyl aminoacid and an ACE inhibitor.

The antihypertensive effect of carboxyalkylcarbonyl aminoacids was determined according to the following procedure:

Male Sprague Dawley rats weighing 100–150 g were anesthetized with ether and the right kidney was removed. Three pellets containing DOC acetate (desoxycorticosterone acetate, DOCA, 25 mg/pellet) were implanted subcutaneously. Animals recovered from surgery, were maintained on normal rat chow and were allowed free access to a fluid of 1% NaCl and 0.2% KCl instead of tap water for a period of 17–30 days. This procedure results in a sustained elevation in blood pressure and is a slight modification of published procedures (e.g. Brock et al., 1982) that have been used to produce DOCA salt hypertension in the rat.

On the day of study, animals were again anesthetized with ether and the caudal artery was cannulated for blood pressure measurement. Patehey of the caudal artery cannula was maintained with a continuous infusion of dextrose in water. at a rate of 0.2 ml/hr. Animals were placed into restraining cages where they recovered consciousness. Blood pressure was measured from caudal artery catheter using a Statham pressure transducer attached to a Beckman oscillographic recorder. In addition, a cardiovascular monitoring device (Buxco Electronics, Inc.) and a digital computer were used to calculate average blood pressures.

After an equilibration period of at least 1.5 hr., animals were dosed subcutaneously (1 ml/kg) with vehicle (methylcellulose, hereinafter MC) or carboxyalkylcarbonyl aminoacid and blood pressure was monitored for the next 4 hours.

A similar procedure can be used to determine the effect of carboxyalkylcarbonyl aminoacid in combination with ACE inhibitors.

The antihypertensive effect of carboxyalkylcarbonyl aminoacids in combination with ANF can be determined according to the following procedures:

Male spontaneously hypertensive rats (SHR), 16-18 weeks old, 270-350 g, are anesthetized with ether and the abdominal aorta is cannulated through the tail artery. The animals are then placed into restrainers to recover from anesthesia (in less than 10 min.) and remain inside throughout the experiments. Through a pressure transducer (Gould P23 series) analog blood pressure signals are registered on a Beckman 612 recorder. A Buxco digital computer is used to obtain mean arterial pressures. Patency of the arterial cannula is maintained with a continuous infusion of 5% dextrose at 0.2 ml/hr. Animals are allowed a 90-min equilibration period. The animals first undergo a challenge with an ANF such as atriopeptin II (AP II) or AP28 30 $\mu$g/kg iv and at the end of 60 min. are treated with drug vehicle or a carboxyalkylcarbonyl aminoacid subcutaneously. A second ANF challenge is administered 15 min. later and blood pressure is monitored for the next 90 min.

The antihypertensive effect in SHR of carboxyalkylcarbonyl aminoacids and ACE inhibitors, alone and in combination, can be determined as follows:

Animals are prepared for blood pressure measurement as described above. After stabilization, animals are dosed subcutaneously or orally with test drugs or placebo and blood pressure is monitored for the next 4 hr.

The compounds having structural formula I have also been found to inhibit the activity of enzymes designated enkephalinases. The compounds are particularly useful for the inhibition of enkephalinase A, which is derived from the striata of both rats and humans. In in vitro tests, using test procedures for enkephalinase A inhibition well known to those skilled in the art, selected compounds having structural formula I have been found to inhibit the activity of the aforementioned enzyme. Therefore, the present invention also relates to a method of inhibiting the action of enkephalinases in a mammal thereby to elicit an analgesic effect with a compound of formula I, and to analgesic pharmaceutical compositions comprising compounds of formula I.

The use of atrial natriuretic peptides in the treatment of nephrotoxicity associated with the immunosuppressive cyclosporin was reported by Capasso et al in the *American Journal of Hypertension*, 3, (1990), p. 204-210. Since compounds of this invention enhance endogenous ANF, they can be used alone to treat nephroxtoxicity, or they can be administered in combination with exogenous ANF.

The compositions Of this invention comprise a carboxyalkylcarbonyl aminoacid or a carboxyalkylcarbonyl aminoacid and an ANF or a carboxyalkylcarbonyl aminoacid and an ACE inhibitor in combination with a pharmaceutically acceptable carrier for administration to mammals. A variety of pharmaceutical forms is suitable, preferably for oral or parenteral administration, although mechanical delivery systems such as transdermal dosage forms are also contemplated.

The daily dose of the compound or combinations of this invention for treatment of hypertension, congestive heart failure, edema or renal insufficiency is as follows: for carboxyalkylcarbonyl aminoacids alone the typical dosage is 1 to 100 mg/kg of mammalian weight per day administered in single or divided dosages; for the combination of carboxyalkylcarbonyl aminoacid and an ANF, the typical dosage is 1 to 100 mg of carboxyalkylcarbonyl aminoacid/kg mammalian weight per day in single or divided dosages plus 0.001 to 0.1 mg ANF/kg of mammalian weight per day, in single or divided dosages, and for the combination of carboxyalkylcarbonyl aminoacid and an ACE inhibitor, the typical dosage is 1 to 100 mg of carboxyalkylcarbonyl aminoacid/kg mammalian weight per day in single or divided dosages plus 0.1 to 30 mg ACE inhibitor/kg of mammalian weight per day in single or divided dosages. The exact dose of any component or combination to be administered is determined by the attending clinician and is dependent on the potency of the compound administered, the age, weight, condition and response of the patient.

Generally, in treating humans having hypertension, congestive heart failure, edema or renal insufficiency, the compounds or combinations of this invention may be administered to patients in a dosage range as follows: for treatment with carboxyalkylcarbonyl aminoacids alone, about 10 to about 500 mg per dose given 1 to 4 times a day, giving a total daily dose of about 10 to 2000 mg per day; for the combination of carboxyalkylcarbonyl aminoacid and ANF, about 10 to about 500 mg carboxyalkylcarbonyl aminoacid per dose given 1 to 4 times a day and about 0.001 to about 1 mg ANF given 1 to 6 times a day (total daily dosage range of 10 to 2000 mg day and 0.001 to 6 mg/day, respectively); and for the combination of a carboxyalkylcarbonyl aminoacid and an ACE inhibitor, about 10 to about 500 mg carboxyalkylcarbonyl aminoacid per dose given 1 to 4 times a day and about 5 to about 50 mg ACE inhibitor given 1 to 3 times a day (total daily dosage range of 10 to 2000 mg/day and 5 to 150 mg/day, respectively). Where the components of a combination are administered separately, the number of doses of each component given per day may not necessarily be the same, e.g. where one component may have a greater duration of activity, and will therefore need to be administered less frequently.

To produce an analgesic effect, compounds of this invention will be administered in a dosage range of from about 1 to about 100 mg/kg. The doses are to be administered at intervals of from 3 to 8 hours. However, the quantity and frequency of dosage will depend upon such factors as the severity of the pain, the general physical condition of the patient, the age and weight of the patient, and other factors recognized by the skilled clinician.

For treatment of edema, renal insufficiency or nephrotoxicity associated with immunosuppressive therapy, dosage ranges for the compounds of this invention are the same as for treatment of hypertension with the use of carboxyalkylcarbonyl aminoacids alone or in combination with ANF.

Typical oral formulations include tablets, capsules, syrups, elixirs and suspensions. Typical injectable formulations include solutions and suspensions.

The typical acceptable pharmaceutical carriers for use in the formulations described above are exemplified by: sugars such as lactose, sucrose, mannitol and sorbitol, starches such as cornstarch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sufate; polyvinylpyrrolidone, polyvinyl alcohol; stearic acid; alkaline earth metal stearates such as magnesium stearate and calcium stearate, stearic acid, vegetable oils such as peanut oil, cottonseed oil, sesame oil, olive oil and corn oil; non-ionic, cationic and anionic surfactants; ethylene gylcol polymers; betacyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

Since the present invention relates to treatment of hypertension with a combination of active ingredients wherein said active ingredients may be administered separately, the invention also relates to combining separate pharmaceutical compositions in kit form. That is, two kits are contemplated, each combining two separate units: a carboxyalkylcarbonyl aminoacid pharmaceutical composition and an ANF pharmaceutical composition in one kit and a carboxyalkylcarbonyl aminoacid pharmaceutical composition and an ACE inhibitor pharmaceutical composition in a second kit. The kit form is particularly advantageous when the separate components must be administered in different dosage forms (e.g. oral and parenteral) or are administered at different dosage intervals.

Following are examples of methods of preparing compounds of formula I.

PREPARATION 1

O-BENZYL-(S)-ISOSERINE ETHYL ESTER pTSA SALT

1. N-(4-Methoxybenzyloxycarbonyl-(S)-isoserine methyl ester

Stir cesium carbonate (6.2 g) and N-(4-methoxybenzyloxycarbonyl-(S)-isoserine (10 g) in dimethyl formamide(DMF) (50 ml) for 1 hr. then add methyl iodide (5.4 g). Stir the resulting mixture for 18 h and concentrate in vacuo. Partition the residue between EtOAc/water and then brine. Concentrate the dried (MgSO4) EtOAc solution in vacuo to give an amber oil. Chromatograph this oil on a column of flash silica gel (1100 ml) using EtOAc:hexane (9:1) as eluant to give an amber oil, $[\alpha]_D^{26} = +16.9°$ (MeOH).

2. N-(4-Methoxybenzyloxycarbonyl-O-benzyl-(S)-isoserine methyl ester

To the product from Step 1, (7.45 g) in anhydrous dimethoxyethane (250 ml), add benzyl bromide (9.3 ml) and silver oxide (9.3 g). Stir the reaction mixture for 72 hr and then heat under reflux for 3 hr. Cool, filter and concentrate in vacuo to give an oil. Chromatograph this oil on flash silica gel (1500 ml) eluting with EtOAc:hexane 2:18 (4 L); 3:17 (4 L); 4:16 (8 L); 5:15 (4 L); 6:14 (4 L) and then EtOAc to give a colorless oil, $[\alpha]_D^{26} = -34.6°$ (MeOH).

3.

To the product from Step 2 (1.2 g) in absolute EtOH (100 ml), add pTSA. H2O (1.3 g) and heat the resulting mixture for 4 hr. Add concentrated HCl (5 drops) and heat the resulting mixture for 34 h. Concentrate the mixture in vacuo to give a tan solid, m.p. 148°–52°, $[\alpha]_D^{26} = -40.4°$ (MeOH).

EXAMPLE 1

N-[1-(2(R,S)-CARBOXY-4-PHENYLBUTYL)CYCLOPENTANECARBONYL]-(L)-METHIONINE 1. 1-(2-t-Butoxycarbonyl-4-phenylbutyl)cyclopentanecarboxylic acid To diisopropylamine (5.13 g, 50.9 mmol) in tetrahydrofuran (THF) (20 ml) at −60° C., add n-BuLi hexane solution (20.3 ml of 2.5M, 50.9 mmol). Warm to 0° C., cool again to −60° C. and add cyclopentanecarboxylic acid (2.89 g, 25.4 mmol). Warm to 0° C. for 2.5 hr., cool again and add t-butyl 2-(2-phenylethyl)acrylate (5.90 g, 25.4 mmol) in THF (10 ml). After 2 h., warm to 0° C., quench with 5N HCl, extract with hexane, wash with 1N NaHCO3, and concentrate to a solid. Chromatograph on silica, eluting with hexane-ether-HOAc 60:40:1 to obtain an oil.

2. N-[1-(2(R,S)-t-Butoxycarbonyl-4-phenylbutyl)cyclopentanecarbonyl]-(S)-methionine ethyl ester Combine the product of Step 1 (1.50 g, 4.33 mmol) with (S)-methionine ethyl ester hydrochloride (0.92 g, 4.33 mmol), triethylamine (0.65 g, 6.5 mmol), hydroxybenzotriazole (HOBT) (0.66 g, 4.33 mmol), and 1-(3-dimethylaminopropyl)- 3-ethylcarbodiimide hydrochloride (DEC) (0.91 g, 4.8 mmol) in 25 ml dimethylformamide (DMF). Stir 18 h., partition between EtOAc-H2O, wash with 1N NaHCO3 and concentrate. Chromatograph the resultant residue on silica, eluting with hexane-ether 1:1 to obtain an oil, $[\alpha]_D^{26} = -17.4°$ (EtOH).

3. N-[1-(2(R,S)-Carboxy-4-phenylbutyl)cyclopentanecarbonyl]-S-methionine ethyl ester Add the product of Step 2 (1.0 g, 2.0 mmol) to trifluoroacetic acid (20 ml). After 45 min., concentrate and partition between Et2O-H2O. Dry and concentrate to obtain an oil, $[\alpha]_D^{26} = -22.6°$ (EtOH).

4.

To the product of Step 3, (0.30 g, 0.61 mmol) in EtOH (30 ml), add 1.0N NaOH (3.0 ml). After 2 hr., concentrate, add 1.0N HCl (3.0 ml) and extract with EtOAc. Dry and concentrate to obtain the title compound as a solid, $[\alpha]_D^{26} = -5.4°$ (EtOH).

EXAMPLE 2

N-[1-(2-(R,S)-CARBOXY-4-PHENYLBUTYL)CYCLOPENTANECARBONYL]-(S)-ISOSERINE

1. N-[1-(2(R,S)-t-Butoxycarbonyl-4-phenylbutyl)cyclopentanecarbonyl]-S-isoserine ethyl ester In a fashion similar to that of Example 1, Step 2, combine the product of Example 1, Step 1 with (S)-isoserine ethyl ester p-toluenesulfonate salt to obtain a colorless foam.

2. N-[1-(2(R,S)-Carboxy-4-phenylbutyl)cyclopentanecarbonyl]-S-isoserine ethyl ester In a fashion similar to that of Example 1, Step 3, treat the product of Step 1 to obtain an oil, $[\alpha]_D^{26} = +8.1°$ (EtOH).

3.

Treat the product of Step 2 in a manner similar to that described in Example 1, Step 4, to obtain the title compound, $[\alpha]_D^{26} = -0.5°$ (EtOH).

EXAMPLE 3

N-[1-[(2(R,S)-CARBOXY)-3-(2-METHOXYETHOXY)PROPYL]CYCLOPENTANECARBONYL]-(S)-METHIONINE

1.

N-[1-[(2(RtS)-t-Butoxycarbonyl)-3-(2-methoxyethoxy)propyl]cyclopentanecarbonyl]-(S)-methionine Ethyl Ester Combine 3-(1-carboxycyclopentyl)-2-(2-methoxyethoxymethyl)-propanoic acid t-butyl ester (1.50 g, 4.6 mmol) with (S)-methionine ethyl ester hydrochloride (0.99 g), N-methylmorpholine (1.0 ml), HOBT (0.71 g), and DEC (1.08 g) in DMF (24 ml). Stir the mixture for 18 hr., concentrate in vacuo, and partition between EtOAc/H2O, then 0.1N HCl, saturated NaHCO3 and brine. Concentrate the dried (MgSO4) EtOAc solution in vacuo to give a light amber oil. Chromatograph the oil on a column of flash silica gel (300 ml) and elute with EtOAc/hexane (1:4) to obtain a colorless viscous oil, $[\alpha]_D^{26} -26.1°$ (MeOH).

2.

N-[1-[(2(R,S)-Carboxy)-3-(2-methoxyethoxy)propyl]cyclopentanecarbonyl]-(S)-methionine Ethyl Ester Combine the product of Step I (0.8 g) with trifluoroacetic acid (5 ml), thioanisole (0.4 ml), and m-cresol (0.4 ml) in CH2Cl2 (15 ml). After 5 hr., concentrate the reaction mixture in vacuo, and chromatograph the resultant residue on silica gel preparative layer plates (10×1000μ) using CH2Cl2/MeOH/NH4OH 170/27/3 as eluant to obtain a viscous oil, $[\alpha]_D^{26} = -26.0°$ (MeOH).

3.

Under a nitrogen atmosphere, dissolve the product of Step 2 (0.42 g, 1.0 mmol) in absolute EtOH (5 ml) and add 1N NaOH (2 ml). After 18 hr., partition the mixture between EtOAc/0.1N HCl (200 ml/500 ml) and then H2O. Concentrate the dried (MgSO4) EtOAc in vacuo to obtain the title compound as a colorless oil, $[\alpha]_D^{26} = -15.9°$ (MeOH).

EXAMPLE 4

N-[1-[2(R,S)-CARBOXY-3-(2-METHOXYETHOXY)PROPYL]CYCLOPENTANECARBONYL]-β-ALANINE BENZYL ESTER

1.

N-[l[2(R,S)-(t-Butoxycarbonyl)-3-(2-methoxyethoxy)propyl]cyclopentyl-1-carbonyl-β-alanine Benzyl Ester Substitute β-alanine benzyl ester p-TSA salt (1.62 g) for the methionine ester in the procedure of Example 3, Step 1, eluting the silica gel with EtOAc/hexane (6:14) to obtain a colorless oil, 491. M+ 491.

2.

Treat the product of Step 1 (1.33 g) with trifluoroacetic acid (5 ml) in CH2Cl2 (15 ml). After 1.5 hr., concentrate the reaction mixture in vacuo, and chromatograph the residue on flash silica gel using CH2Cl2/MeOH/NH4OH 170/27/3 as eluant and on silica gel preparative layer plates (12×1000μ) using CH2Cl2/MeOH/NH4OH 170/27/3 as eluant to obtain the title compound as a viscous oil.

EXAMPLE 5

N-[1-[(2(R,S)-CARBOXY)-3-(2-METHOXYETHOXY)PROPYL]CYCLOPENTANECARBONYL]-(S)-ISOSERINE BENZYL ESTER

1.

N-[1-[(2(R,S)-t-Butoxycarbonyl)-3-(2-methoxyethoxy)propyl]cyclopentanecarbonyl]-(S)-isoserine Benzyl Ester In a manner similar to that described in Example 3, Step 1, substitute (S)-isoserine benzyl ester hydrochloride for the methionine compound and elute the silica gel with EtOAc/hexane (7:13) to obtain a colorless oil, $[\alpha]_D^{26} = +10.4°$ (MeOH).

2.

Treat the product of Step 1 (1.04 g) with trifluoroacetic acid (20 ml) in CH2Cl2 (20 ml). After 18 hr., concentrate the reaction mixture in vacuo, and chromatograph the residue on silica gel preparative layer plates (12×1000μ) using CH2Cl2/MeOH/NH4OH 170/27/3 as eluant to obtain the title compound as a viscous oil, $[\alpha]_D^{26} = +8.1°$ (MeOH).

EXAMPLE 6

N-[1-[2(R,S)-CARBOXY-3-(2-METHOXYETHOXY)PROPYL]CYCLOPENTANECARBONYL]-O-BENZYL-(S)-ISOSERINE

1.

N-[1-[2(R,S)-(t-Butoxycarbonyl)-3-(2-methoxyethoxy)propyl]cyclopentanecarbonyl]-O-benzyl-(S)-isoserine ethyl ester Substitute O-benzyl-(S)-isoserine ethyl ester p-TSA salt (0.75 g) for the methionine ester in the procedure of Example 3, Step 1, and elute the silica gel with EtOAc/hexane (1:3) to obtain a colorless oil, $[\alpha]_D^{26} = -21.7°$ (MeOH).

2.

N-[1-[2(R,S)-Carboxy-3-(2-methoxyethoxy)propyl]cyclopentanecarbonyl]-O-benzyl-(S)-isoserine ethyl ester Treat the product of Step 1 (0.60 g) with trifluoroacetic acid (10 ml) in CH2Cl2 (10 ml). After 0.5 hr., concentrate the reaction mixture in vacuo to give a colorless oil, $[\alpha]_D^{26} = -23.8°$ (MeOH).

3.

In a manner-similar to that described in Example 3, Step 3, substitute the product from Step 2 above (0.271 g) for the methinonine compound to give the title compound as a viscous colorless oil, $[\alpha]_D^{26} = -37.8°$ (MeOH).

The following formulations exemplify some of the dosage forms of the compositions of this invention. In each, the term "active compound" designates a compound of formula I, preferably N-[1-(2-carboxy-4- phenylbutyl)cyclopentanecarbonyl]-(S)-isoserine. However, this compound may be replaced by equally effective amounts of other compounds of formula I.

Pharmaceutical Dosage Form Examples

Example A

| | Tablets | | |
|---|---|---|---|
| No. | Ingredient | mg/tablet | mg/tablet |
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1minutes. Compress the mixture to appropriate size and weight on a suitable tablet machine.

Example B

| | Capsules | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | TOTAL | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

Example C

| Parenteral Preparation | | |
|---|---|---|
| Ingredient | mg/vial | mg/vial |
| Active Compound Sterile Powder | 100 | 500 |

For reconstitution add sterile water for injection or bacteriostatic water for injection.

We claim:

1. A compound represented by the formula

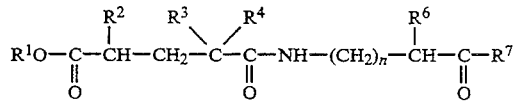

wherein $R^1$ is H;

$R^2$ is alkyl substituted with alkoxy, alkoxyalkoxy, or phenyl;

$R^3$ and $R^4$ together with the carbon to which they are attached form a 5-, 6- or 7-membered carbocyclic ring;

n is 0, 1, 2 or 3;

$R^6$ is alkylthioalkyl, and when n is 1,2 or 3, $R^6$ is also hydroxy or benzyloxy; and $R^7$ is hydroxy, alkoxy or phenylalkoxy; or a pharmaceutically acceptable salt thereof.

2. A compound of claim 1 wherein $R^2$ is phenylalkyl or alkoxyalkoxyalkyl.

3. A compound of claim 1 wherein $R^6$ is alkylthioalkyl and n is zero.

4. A compound of claim 1 wherein $R^1$ is hydrogen and $R^7$ is hydroxy or benzyloxy.

5. A pharmaceutical composition for treating hypertension comprising 10 to 500 mg of a compound of claim 1 in a pharmaceutically acceptable carrier.

6. A method for treating hypertension in mammals comprising administering to a mammal in need of such treatment an effective amount of a compound of claim 1.

7. A compound of claim 1 wherein $R^6$ is hydroxy and n is 1.

8. A compound of claim 1 which is

N-(1-(2-carboxy-4-phenylbutyl)cyclopentanecarbonyl)-(L)-methionine;

N-(1-(2-carboxy-4-phenylbutyl)cyclopentanecarbonyl)-(L)-methionine ethyl ester;

N-(1-(2-carboxy-4-phenylbutyl)cyclopentanecarbonyl)-(S)-isoserine;

N-(1-(2-carboxy-4-phenylbutyl)cyclopentanecarbonyl)-(S)-isoserine ethyl ester;

N-(1-(2-carboxy-3-(2-methoxyethoxy)propyl)cyclopentanecarbonyl)-(S)-methionine;

N-(1-(2-carboxy-3-(2-methoxyethoxy)propyl)cyclopentanecarbonyl)-(S)-methionine ethyl ester;

N-(1-(2-carboxy-3-(2-methoxyethoxy)propyl)cyclopentanecarbonyl)-(S)-isoserine benzyl ester;

N-(1-(2-carboxy-3-(2-methoxyethoxy)propyl)cyclopentanecarbonyl)-O-benzyl-(S)-isoserine ethyl ester;

N-(1-(2-carboxy-3-(2-methoxyethoxy)propyl)cyclopentanecarbonyl)-O-benzyl-(S)-isoserine.

* * * * *